United States Patent [19]
LaCroix et al.

[11] Patent Number: 5,968,913
[45] Date of Patent: Oct. 19, 1999

[54] PHARMACEUTICAL COMPOSITIONS OF URIDINE TRIPHOSPHATE

[75] Inventors: Karol K. LaCroix, Holly Springs; Christy L. Shaffer, Chapel Hill; Karla M. Jacobus, Carey; Janet L. Rideout, Raleigh; David J. Drutz, Chapel Hill; Richard C. Evans, Carey; William Pendergast, Durham, all of N.C.

[73] Assignee: Inspire Pharmaceuticals, Inc., Durham, N.C.

[21] Appl. No.: 08/996,740

[22] Filed: Dec. 23, 1997

Related U.S. Application Data

[63] Continuation-in-part of application No. 08/675,555, Jul. 3, 1996, abandoned.
[51] Int. Cl.⁶ .............................. A61K 9/08; A61K 31/70
[52] U.S. Cl. ................................ 514/47; 424/45; 424/47
[58] Field of Search ........................... 424/45–47; 514/47

[56] References Cited

U.S. PATENT DOCUMENTS

| | | | |
|---|---|---|---|
| 4,758,553 | 7/1988 | Ogoshi | 514/47 |
| 5,164,740 | 11/1992 | Ivri | 346/1.1 |
| 5,292,498 | 3/1994 | Boucher, I | 424/45 |
| 5,420,116 | 5/1995 | Puchelle et al. | 514/47 |
| 5,518,179 | 5/1996 | Humberstone et al. | 239/102.2 |
| 5,544,646 | 8/1996 | Lloyd et al. | 128/200.14 |
| 5,547,131 | 8/1996 | Brace | 239/309 |
| 5,593,824 | 1/1997 | Treml et al. | 435/4 |
| 5,628,984 | 5/1997 | Boucher, II | 424/45 |

FOREIGN PATENT DOCUMENTS

| | | | |
|---|---|---|---|
| 597360 | 3/1961 | Belgium . | |
| 2677250 | 5/1991 | France . | |
| 92 11016 A1 | 7/1992 | WIPO . | |
| WO 92/11016 | 7/1992 | WIPO . | |
| 97 05195 A1 | 2/1997 | WIPO | 509/52 |
| 97 29756 A1 | 8/1997 | WIPO | 604/463 |
| 97 35591 A1 | 10/1997 | WIPO | 624/914 |
| 97 35591 A2 | 10/1997 | WIPO | 624/914 |
| 98 03182 A2 | 1/1998 | WIPO | 685/216 |
| 98 19685 A1 | 5/1998 | WIPO | 744/367 |

OTHER PUBLICATIONS

Bouchere, R. et al., "Mechanisms and Therapeutic Actions of Uridine Triphosphate in the Lung" Adenosine and Adenine Nucleotides: From Molecular Biology to Integrative Physiology. Editors Beladinelli & A Pellg. Ahlwer Academic Publishers, Boston pp. 525–532 (1995).

Drutz, D. et al., "Uridine 5' Triphosphate (UTP) Regulates Mucociliary Clearance Via Purinergic Receptor Acitvation," Drug Developmental Research 337(3) 185 (1996).

Fischer, B. et al., "Identification of Potent, Selective $P_{2y}$–Purinoceptor Agonists: Structure–Activity Relationships for 2–Thioether Derivatives of Adenosine 5'–Triphosphate," J. Med. Chem. 36:3937–3946 (1993).

Gobran, L. et al., "$P_{2u}$ purinoceptor stimulation of surfactant secretion coupled to phosphatidylcholine hydrolysis in type II cells," Am J. Physiol. 267:L625–L633 (1994).

Hoard, D. and Ott, D., "Conversion of Mono– and Oligodeoxyribonucleotides to 5'–Triphosphates," J Am. Chem. Soc. 87:1785–1788 (1965).

Lethem, M. et al., "Nucleotide Regulation of Goblet Cells in Human Airway Epithelial Explants Normal Exocytosis in Cystic Fibrosis," Am J. Respir. Cell Mol. Biol. 9:315–322 (1993).

Noone, P. et al., "Effects on Cough Clearance of Aerosolized Uridine–5'–Triphosphate±Amiloride in Patients with Primary Ciliary Dyskinesia," Am. J. Resp. Crit. Care Med. A530 (1996).

Rooney, S. et al., "Signal Transduction Mechanisms Mediating Surfactant Phospholipid Secretion in Isolated Type II Cells," Prog. Respir. Res. 27:84–91 (1994).

Yoshikawa, M. et al., "A Novel Method for Phosphorylation of Nucleosides to 5'–Nucleotides," Tetrahedron Let. (50)5065–5068 (1967) and Bull. Chem. Soc. (83)649–659 (1961).

Knowles et al Chest 107/2 715–765 Pharmacology Treatment of Abnormal Ion Transport in the Airway Opithelium in Cystic Fibrosis Aerosolized Ltd., 1995.

Harris et al Curr. Opin. Pediatr 6/3:234–238 Inhalation–Based Therapies in the Treatment of Cystic Fibrosis Nebulizor Aerosolized Ltd., 1994.

Noone et al Monald Archiugs for Chest Disease 48(2) 140–143 Trends in Therapy of Abnormal Airway Epithel VTP Repel, 1993.

Primary Examiner—Shep K. Rose
Attorney, Agent, or Firm—Albert P. Halluin; John A. Bendrick; Howrey & Simon

[57] ABSTRACT

Novel pharmaceutical compositions of uridine 5'-triphosphate (UTP) for use in promoting increased mucociliary clearance of retained mucous secretions of the human airways, middle/inner ears or sinuses are disclosed. Novel Formulation I comprises UTP and aqueous solution having a therapeutic concentration between 5 and 45 mg/mL, a controlled tonicity within the range of 250 to 100 mOsM, a pH between 7.0 and 7.5, and is sterile. The pH-adjusted composition is capable of long-term storage in the refrigerated state with a shelf life of up to 30 months. Formulation I may be delivered therapeutically either in a nebulized form or in a liquid form. Novel Formulation II comprises UTP in an aqueous solution or suspension having a therapeutic concentration approaching the limit of UTP's solubility at ambient temperature. This high concentration allows delivery of a therapeutic amount of UTP in very small volumes (50 to 100 $\mu$L) suitable for administration via portable hand-held devices such as metered dose inhalers. Formulation II has extended shelf life without the need for refrigeration after being dispensed to the patient.

6 Claims, 6 Drawing Sheets

PHARMACEUTICAL COMPOSITIONS OF URIDINE TRIPHOSPHATE

This is a continuation-in-part of U.S. application Ser. No. 08/675,555 filed Jul. 3, 1996 abandoned, which is incorporated herein by reference.

TECHNICAL FIELD

This invention relates to novel pharmaceutical compositions of uridine 5'-triphosphate (UTP). The compositions are effective for promoting mucociliary clearance of retained mucous secretions in mammalian airways, middle/inner ears or sinuses. The compositions are capable of both therapeutic and diagnostic applications.

BACKGROUND OF THE INVENTION

Mucociliary clearance is an important defense mechanism of the human airways and middle/inner ear tract. Coordinated beats of cilia in the airways and ears propel the mucous layer toward the pharynx, carrying along with it microorganisms and other particles captured in the mucus. Normal function of this system depends on the frequency and coordination of ciliary beating and the properties of the mucus itself.

It has been discovered that extracellular nucleoside triphosphates, especially UTP, modulate mucociliary clearance. Specifically, UTP stimulates ciliary beat frequency (D. Drutz, et al., Drug Development Research, 377(3), 185, (1996)), increases hydration of the mucous layer on the luminal surface of the airway (R. Boucher, et al., Adenosine and Adenine Nucleotides: From Molecular Biology to Integrative Physiology, p. 525–32 "Mechanisms and Therapeutic Actions of Uridine Triphosphates in the Lung" (L. Belardinelli, et al. ed., Alumwer Academic Publishers, Boston, 1995)), and increases mucin release from goblet cells and submucosal glands (M. I. Lethem, et al., Nucleotide regulation of goblet cells in human airway epithelial explants: normal exocytosis in cystic fibrosis. Am. J. Respir. Cell Mol. Biol., 1993; 9:315–322. In addition, UTP and other nucleotides have been shown to stimulate the release of surfactant phospholipids from type II alveolar cells (S. Rooney, et al., Progr. Respir. Res., 27, 84–91 (1994); L. Gobran, et al., Am. J. Physiol., 267, L625–33 (1994). It has been postulated that UTP is effective in the treatment of cystic fibrosis and other airway diseases involving retained mucous secretions as described in U.S. Pat. No. 5,292,498 and U.S. Pat. No. 5,420,116. It has also been demonstrated that UTP is safe and improves cough clearance in PCD patients (P. Noone, et al., Am. J. Resp. Crit Care Med A530, (1996)). Inspire Pharmaceuticals, Inc. (Durham, N.C.) studies have demonstrated that UTP helps induce a sputum sample by hydrating mucous secretions and stimulating ciliary beat frequency for diagnostic analysis, such as cytopathology for lung cancer or acid-fast bacillus for tuberculosis. It is likely that UTP decreases the risk of retained secretions in patients who are immobilized or receiving mechanical ventilation, thereby preventing pneumonia, including ventilator-associated pneumonia (VAP).

A UTP formulation under the tradename Uteplex®, with a pH of 9.0, has been marketed in France by Wyeth for the treatment of lower backpain. The French biotechnology company Synthelabo has developed a formulation of adenosine triphosphate (ATP) under the tradename rhinATP™ for the treatment of nasal mucous fluid congestion. Belgium Patent No. 597,360, issued Dec. 14, 1960, entitled "Novel Therapeutic Composition Usable as a Muscle and Nerve Stimulant", describes a formulation of UTP used in various myopathies and in nerve stimulation therapy.

With the prospect of increasing clinical uses of UTP on the horizon, the need for more biocompatible and less temperature sensitive formulations has emerged.

Formulation I of the present invention differs from prior art nucleotide pharmaceutical formulations in that it is sterilized by filtration rather than by heat, it has a controlled tonicity within the osmolarity range of 250 to 1000 mOsM, most preferably approximately 300 mOsM, and it is pH-adjusted to give values in the range of 6.5 to 8.5, preferably 6.5 to 8.0 and most preferably 7.0 to 7.5. An unexpected property of the present invention is that the Formulation I is capable of extended shelf-life if kept properly refrigerated. This novel UTP Formulation I is compatible for use in a commercially available nebulizer (e.g., jet nebulizers, ultrasonic nebulizers, etc.) which facilitate their administration in the clinical setting. The liquid UTP Formulation I of the present invention may be delivered to the airways of a patient via inhalation of a nebulized form or it may be delivered to the nose, eye, sinuses or middle/inner ears by means of nasal, eye or ear drops. In either the nebulized or liquefied forms, an effective amount of UTP contacts the affected site directly.

Formulation II of the present invention differs from prior art nucleotide formulations in that it is particularly well-suited for administration via small, portable hand-held devices that are capable of efficiently generating fine respirable aqueous based aerosols from small pre-measured volumes or metering a small volume from a liquid reservoir prior to administration. Suitable devices for the administration of Formulation II include, but are not limited to, those currently in development by the Aradigm Corporation (Hayward, Calif.) as disclosed in U.S. Pat. No. 5,544,646 by Aerogen, formerly Fluid Propulsion Technology as disclosed in U.S. Pat. No. 5,164,740, and by the Technology Partnership (Hertfordshire, UK) as disclosed in U.S. Pat. No. 5,518,179. In addition, small volume topical delivery metered pump based systems, such as that patented by Bespak plc, UK disclosed in U.S. Pat. No. 5,547,131, may be used to deliver Formulation II of the present invention via the nose or ear.

SUMMARY OF THE INVENTION

Novel pharmaceutical compositions of UTP are disclosed. The compositions comprise a UTP raw material, e.g., uridine 5'-triphosphate trisodium salt dihydrate, in a sterile aqueous solution or suspension. Formulation I is sterilized, of controlled tonicity, pH-adjusted and capable of extended shelf life when kept properly refrigerated. It is compatible for use in a variety of commercially available nebulizers, such as jet or ultrasonic nebulizers.

Formulation II is highly concentrated and suitable for administration via a small, portable hand-held devices that are capable of efficiently generating fine respirable aqueous based aerosols from small pre-measured volumes or of metering a small volume from a liquid reservoir. Additionally, Formulation II is also well suited for topical delivery of small volumes via metered pump based systems which would deliver a therapeutically effective amount of UTP via the nose or ear.

These novel formulations of UTP are well suited to be therapeutically administered in order to promote mucociliary clearance in patients suffering from retained mucous secretions in the lungs, sinuses or middle/inner ears; increase expectoration and sputum production to induce sputum for the purposes of diagnostic analysis, clear the lungs of various airborne toxins, clear the lungs prior to radiological imaging and clear the lungs prior to vaccination or gene therapy.

The formulations of the present invention also encompasses the pharmaceutically acceptable salts of UTP, e.g., an alkali metal salt such a sodium or potassium; an alkaline earth salt; or an ammonium or tetraalkyl ammonium salt i.e., $NX_4^+$ wherein X is $C_{1-4}$.

Because UTP is heat labile, Formulations I and II of the present invention are sterilized by filtration rather than by heat.

A second aspect of the present invention is that the tonicity of Formulation I can be controlled, e.g., for an isotonic formulation; thus $UTPNa_3$ is dissolved in the appropriate amount of saline or other aqueous solution to control tonicity within the osmolarity range of 250 to 1000 mOsM; the preferred osmolarity level is between 250 to 450 mOsM; the most preferred osmolarity is approximately 300 mOsM, i.e., an isotonic solution.

A third aspect of the present invention is that Formulation I is pH-adjusted to be in the range of 6.0 to 8.5; the preferred pH level is between 7.0 and 7.5.

A fourth aspect of the present invention is that Formulation I may be formulated in multiple concentrations of UTP between 0.1 and 100 mg/mL; the preferred therapeutic UTP concentration is between 5 and 45 mg/mL.

A fifth aspect of the present invention is that Formulation I with a pH value of 7.0 to 7.5 will remain in stable form for up to 30 months when stored at a temperature between 0° to 10° C. The preferred storage temperature is approximately 5° C.

In a sixth aspect of the present invention, Formulation II is highly concentrated, either approaching the limit of solubility of UTP over a temperature range of −20° to +40° C., or as a microfine particulate suspension.

In a seventh aspect of the present invention, a very small volume of Formulation II can be administered while maintaining therapeutic efficacy. The volume range of this highly concentrated UTP Formulation Is from 10 to 1000 μL, preferably 25 to 500 μL and most preferable 50 to 100 μL.

In an eighth aspect of the present invention, since Formulation II is delivered to the target site and is rapidly diluted by airways surface liquid, there is no need to maintain the osmolality of this Formulation It a physiologically isotonic value or to maintain a physiological pH.

In a ninth aspect of the present invention, Formulation II does not need refrigeration once it has been dispensed to the patient.

In a tenth aspect of the present invention, Formulation II does not require inclusion of a preservative.

DESCRIPTION OF THE SPECIFIC EMBODIMENT

The pharmaceutical compositions of the present invention are novel formulations of UTP and sterile aqueous solution which are well suited for clinical therapeutic administration.

Formulation I is sterilized, has a controlled tonicity, is pH-adjusted, and is compatible for administration in a variety of commercially available nebulizers, such as jet or ultrasonic nebulizers. An unexpected property of Formulation I is that it is capable of extended shelf life when stored in a refrigerated state.

Formulation II is highly concentrated, and a very small volume can be delivered to the target and still be therapeutically effective. An unexpected property of Formulation II is that there is no need to include a preservative.

The therapeutic purpose of the pharmaceutical compositions of the present invention, Formulation I and Formulation II, is to increase mucociliary clearance of retained mucous secretions from the airways, lungs, sinuses and middle/inner ears and eyes of patients suffering from cystic fibrosis, bronchitis, sinusitis, otitis media, primary ciliary dyskinesia, ventilator-associated pneumonia and other diseases involving retained mucous secretions or impaired ciliary movement, as well as bed ridden individuals not suffering from any diseases but who have a high risk of accumulating mucous secretions, e.g., quadriplegics. Formulation I and Formulation II also improve expectoration and the induction of sputum samples for diagnostic analysis, e.g., for diagnosis of lung cancer, tuberculosis or other lung diseases.

Additionally, because of the well demonstrated ability of UTP, the active compound of the present pharmaceutical compositions, to enhance lung mucociliary clearance in normal subjects, the formulations of the present invention may be used to accelerate the clearance of any type of inhaled foreign material from the airways. This would prove beneficial in a number of situations, e.g., biological warfare, smoke inhalation, industrial and mining exposure to inhaled toxins (resulting in silicosis, anthracosis and the gamut of so-called pneumoconiosis); inhaled radiolabel or other diagnostic imaging agent, and allergic reaction to inhaled particles such as pollen.

The pharmaceutical compositions of the present invention are primarily intended for administration to a human subject, but they may also be administered to other mammalian subjects, such as dogs, cats and horses for veterinary purposes.

Formulation I may be administered to the lungs or nose in a nebulized form which the patient inhales, or it may be administered in a liquid form, e.g., nose, eye or ear drops. With either the nebulized or liquid form, an effective amount of UTP contacts the affected site directly.

Formulation II may be administered to the lungs, nose or ears via small, portable, hand-held devices which are capable of efficiently generating fine respirable aqueous aerosols from small premeasured volumes or by metering a small volume from a liquid reservoir. Suitable hand-held devices include, but are not limited to, those currently in development by Aradigm Corp., Aerogen Corporation, formerly Fluid Propulsion Technology, and by the Technology Partnership. In addition, small volume topical delivery systems based on a metered pump (such as that patented by Bespak plc) may be used to deliver Formulation II. Whether administration is via a portable hand-held device or a topical delivery metered pump system, an effective amount of UTP contacts the affected site.

The formulations of the present invention also encompass the pharmaceutically acceptable salts of UTP, e.g., an alkali metal salt such a sodium or potassium; an alkaline earth salt; or an ammonium or tetraalkyl ammonium salt i.e., $NX_4^+$ wherein X is $C_{1-4}$. Pharmaceutically acceptable salts are salts that retain the desired biological activity of the parent compound and do not impart undesired toxicological effects.

The raw material for the pharmaceutical compositions of the present invention, e.g., $UTPNa_3$ dihydrate, may be made in accordance with known procedures or variations thereof which will be apparent to those skilled in the art. For example, phosphorylation of nucleosides can be accomplished by standard methods such as described in D. Hoard and D. Ott, J. Am. Chem. Soc. 87, 1785–88 (1965); M. Yoshikawa et al., Tetrahedron Let. 5065–68 (1967) and Bull. Chem. Soc. 83, 649–59 (1961); and B. Fischer et al., J. Med. Chem. 36, 3937–46 (1993) and references therein. UTP is also commercially available (Sigma, St. Louis, Mo., USA).

To increase the stability of the solid drug substance, UTP in powder form may be kept frozen at a temperature between −20° and −80° C. and in such circumstances should be allowed to warm to room temperature prior to the formulation procedure. Additionally, the UTP raw material should be brought to handling temperature before opening to minimize water absorption and/or condensation of moisture present in ambient air.

The tonicity of Formulation I of the present invention may be controlled by adding a sterile aqueous solution, e.g., saline solution, to dry powder $UTPNa_3$ by techniques known to those skilled in the art to bring the tonicity to any desired level of osmolarity within the range of 250 to 1000 mOsM; preferably the osmolarity of the solution is within the range of 250 to 450 mOsM; most preferably the solution is isotonic with biologic fluids, i.e., the osmolarity is approximately 300 mOsM. The solution is pH-adjusted by techniques known to those skilled in the art such that the pH of said solution is between 6.0 and 8.5; preferably the pH is between 7.0 and 7.5. The solution is then sterilized by filtration, using an appropriate micron filter.

An unexpected result of the present invention is that isotonic, pH-adjusted and sterilized UTP Formulation I remained in stable form for up to 30 months when stored at a temperature between 0° to 10° C. Formulation I of the present invention confers a practical benefit in that valuable freezer space is not required.

Formulation I may be prepared at multiple concentrations of UTP between 0.1 and 100 mg/mL; the preferred therapeutic concentration of UTP is between 5 and 45 mg/mL.

Clinical administration of Formulation I is facilitated because it is suitable for administration utilizing most commercially available nebulizers, e.g., the Pari LC Plus jet nebulizer.

For Formulation II, the concentration of the pharmaceutical composition can be controlled by adding a sterile aqueous or ethanolic solution to dry powder $UTPNa_3$ by techniques known to those skilled in the art to bring the concentration to about 1 g/mL, the limit of its solubility under ambient conditions. The concentration of a microfine particulate suspension can also deliver a therapeutic dose of UTP.

Formulation II, because of its high concentration of UTP, delivers a therapeutic dose of UTP with a volume range of only 10 to 1000 $\mu L$, with a preferred range of 25 to 500 $\mu L$ and a most preferred range of 50 to 100 $\mu L$.

Since a very small volume of solution of Formulation II is delivered to the target site, it is immediately diluted by airways surface liquid, eliminating the need to maintain osmolarity at a physiologically isotonic value. Similarly, a more basic pH solution can be tolerated by the patient The pH range of Formulation II may be between 6.5 and 12; preferably between 7.5 and 12; more preferably between 7.5 and 12; more preferably between 7.5 and 11; even more preferably between 7 and 10; most preferably between 8 and 10, and optimally between 7 and 9.

An unexpected advantage of Formulation II is that its higher pH and the non-concentrafion dependent degradation of UTP in solution result in a pharmaceutical composition that does not have to be refrigerated once dispensed to the patient.

The delivery of a dose of UTP from a sealed, premeasured unit volume of solution is preferred, because there is no need to include a preservative in the formulation. However, a reservoir system, from which a small volume is metered and aerosolized is also acceptable for drug delivery. For a reservoir system, a single preservative or a combination of preservatives may be required depending upon the osmolarity and/or pH of the solution. Acceptable preservatives include, but are not limited to, chlorobutanol or benzalkonium chloride.

The pharmaceutical compositions of the present invention are explained in greater detail in the Examples which follow. These Examples are intended to be illustrative of the invention and are not to be taken as limiting thereof.

EXPERIMENTAL EXAMPLES

Example 1

Formulation I (6 Liter Pilot GMP Batch)

Prior to formulation $UTPNa_3$ dihydrate was kept frozen at −20° C. The UTP powder was allowed to warm to handling temperature for at least one hour prior to opening; this is to minimize water absorption. The UTP raw material was dissolved in sterile aqueous solution (saline solution). An appropriate concentration of saline solution was used to bring osmolarity to approximately 300 mOsM, i.e., an isotonic solution. Alternatively, UTP powder can be dissolved in sterile water and an appropriate amount of NaCl added to bring the osmolarity to approximately 300 mOsM. In either case, aqueous solution was added in sufficient volume to reach an optimum therapeutic UTP concentration level of 5 to 45 mg/mL. The liquid solution was pH-adjusted to bring the pH level to between 7.0 to 7.5. The resulting UTP solution was sterilized by filtration with a $0.2\mu$ filter. Quality control tests were performed prior to packaging: bacteriostasis/fungistasis; endotoxin assay; high-pressure liquid chromatography, osmolarity assay; pH-level assay; concentration assay; and visual inspection for particulate matter. Rejected vials were destroyed.

Approximately 1250 vial containers were then filled per 6-liter batch to a level of 4.2 mL each, with a fill target of 4.4 mL (the label claim is 4.0 mL). Vials are shipped within two weeks of manufacture.

Example 2

Formulation II (5 L Batch 250 and 300 mg/mL)

A vessel was filled with 4500 mL of Cool water for injection, USP (WFI) for 250 and for 300 mg/mL strengths. The Cool WFI temperature was 2° to 8° C. A calculated amount of $UTPNa_3$ dihydrate was weighed and added to the mixing vessel and the mixture was stirred until $UTPNa_3$ was dissolved. The pH was checked (limit between 8 and 10; target 9.0). A 1 N solution of sodium hydroxide was prepared, and the pH of the UTP solution was adjusted by adding sodium hydroxide to pH 8.8 to 9.2 (target 9.0). If the pH exceeded 9.2, 250 mL of 0.1 N hydrochloric acid solution was prepared by filling a 300 L glass flask with 247.5 g WFI, adding 2.5 g of hydrochloric acid NF, and mixing for 5 minutes. The 0.1 N hydrochloric acid solution was added to the UTP solution until the pH was 8.8 to 9.2 (target 9.0).

Qs. solution to the following amounts, based upon a theoretical calculation of densities of 1.1534 and 1.1834 mg/mL for 250 and 300 mg/mL strengths, respectively:

| Strength | Volume |
|---|---|
| 250.0 mg/mL | 5,767 g |
| 300.0 mg/mL | 5,917 g |

The solutions were submitted to the quality control laboratory for determination of potency, osmolarity, pH and density. The mixing vessels were sealed. If overnight storage was required, the mixing vessels were transferred to a refrigerator and stored at 2° to 8° C. After removing from the refrigerator, the batches were mixed an additional ten minutes. Filter assembly and pump were attached to each vessel, and a 0.2 micron filter was connected to the receiving vessel. After product filtration was complete, post-fill integrity was performed into the receiving vessel. The product vessel was connected to filling equipment, and the fill volume was adjusted to 50 $\mu$L (+, -) 5 $\mu$L.

Clinical Studies

A. Normal Healthy Volunteers (Non-Smokers)

Study Design: This single-center Phase I Unit study was a randomized, double-blind evaluation of escalating, single doses of aerosolized UTP in 48 healthy male volunteers. Four successive groups of 12 volunteers were enrolled at each dose level and were randomized in a 2:1 fashion to receive UTP or placebo. Placebo was normal saline, and the four dose levels of UTP evaluated were: 0.5 mg/mL, 5 mg/mL, 25 mg/mL and 45 mg/mL. At the time of dosing, 4 mL of placebo or 4 mL of the appropriate UTP solutions were placed in a nebulizer for aerosolization. The purpose of this study was to determine safety and tolerability of UTP at various dose levels and to determine if UTP could enhance the ability of normal, healthy subjects to expectorate sputum containing alveolar macrophages, cells indicative of a deep lung sample, when compared to placebo.

Treatments Assignments and Administration of Study Drug: Each subject was randomly assigned to receive a single dose of either UTP or placebo. Each dose consisted of 4 mL of placebo or the appropriate solution of UTP (0.5, 5, 25, or 45 mg/mL) and was administered using a jet nebulizer (Pari LC PLUS™) powered by portable compressor (DeVilbiss Pulmo-Aide®) set at a flow rate of 14 L/min. Inhalation of placebo or UTP took approximately 8 to 15 minutes.

Investigational Products: The test product was UTP Solution for Inhalation in a concentration of 0.5, 5, 25 or 45 mg/mL. UTP solutions were packaged in single use glass vials with rubber stoppers and aluminum tear-off seals. The product was stored refrigerated at 2°–8° C. Each vial delivered 4 mL of solution upon pouring. The pH of each solution was 7.2 and the tonicity of each solution was approximately 300 MOsm/L. Each vial was individually labeled with the contents, strength and storage instructions.

The placebo was supplied as sterile Sodium Chloride Inhalation Solution USP, 0.9% (Dey Laboratories, Napa Calif., USA). Placebo was packaged in single use vials containing 5 mL of solution. Per USP specifications, the pH of the solution was within the range of 4.5–7.0. Four mL of placebo was used for administration. The product was stored at 2°–8° C. Each vial was individually labeled with contents, strength and storage instructions.

Efficacy Results: Sputum was collected for the purpose of cytological examination to determine whether the sample contained alveolar macrophages. The presence of alveolar macrophages in a sputum sample indicates that the sample is a quality specimen arising from deep within the lungs (not simply salivary secretions). For this study, sputum was collected for cytological examination at the following times: baseline (pre-dose), immediately post-dosing, post-dosing to 4 hours, 4 hours to 8 hours post-dosing, 8 hours to 12 hours post-dosing and upon rising the following day.

Figure 1:
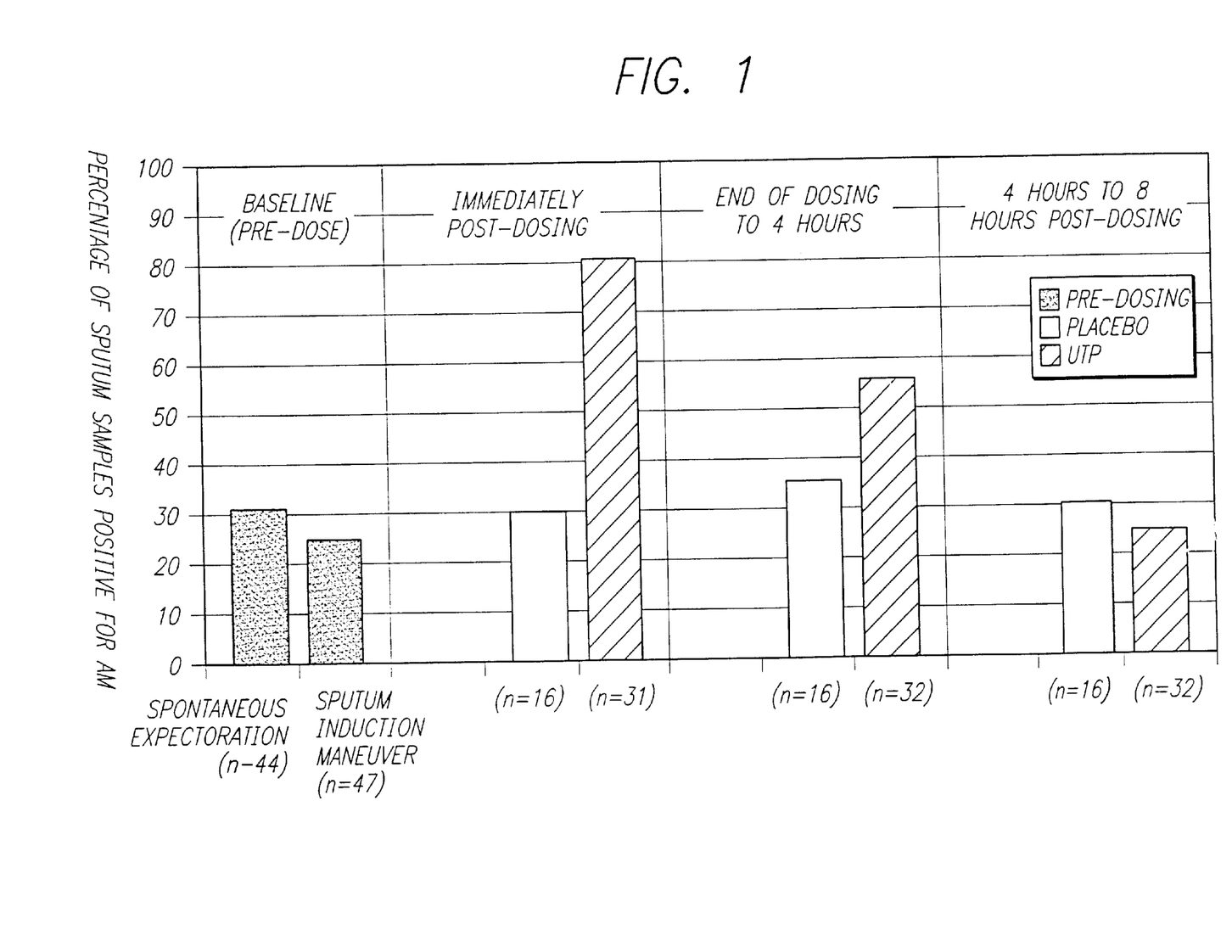
FIG. 1 is a general graphical representation of the time-course for the effect of UTP Formulation I versus placebo on the percentage of sputum samples positive for alveolar macrophages (AMs) in non-smokers.

For purposes of data analysis, all patients receiving placebo were combined (n=16) and patients receiving UTP (n=32, all four dose levels) were combined. Data from all 48 subjects were combined for the baseline sputum sample time point. FIG. 1 illustrates the time course for the effect of placebo and UTP on the percentage of sputum samples determined to be positive for alveolar macrophages (AM). Although the majority of the subjects (pre-dose period) could produce a sputum sample at baseline (44/48 subjects spontaneously and 47/48 subjects produced a sample following a simple maneuver involving 3 deep breaths, followed by a cough); only about 30% of these samples were considered to be a quality sputum sample as evidenced by cytological examination (presence of AMs). Aerosolization of single dose of placebo (normal saline) in 16 subjects failed to improve the percentage of samples determined to contain alveolar macrophages at the immediately post-dosing time point compared to baseline. However, in the UTP combined group (n=32), over 80% of the sputum samples were considered positive for alveolar macrophages, representing a 2.5 fold improvement over baseline and placebo. The effect of UTP to improve the percentage of samples positive for alveolar macrophages was also evident at the second time point (end of dosing to 4 hours post-dosing); 37% of samples were positive following administration of placebo versus 57% following UTP. The differences observed between UTP and placebo were no longer evident by the 4 hour to 8 hour time point at which point both the placebo and UTP groups were essentially the same as the pre-dose values. This is consistent with the relatively short duration of action of UTP as well as findings in a previous study indicating that single, inhaled doses of UTP enhance whole lung mucociliary clearance for about 1.5 hours.

B. Smokers Study

Study Design: This second study in smokers was a single-center, randomized, double-blind, cross-over evaluation of multiple daily doses of the highest dose level of aerosolized UTP evaluated in the previous study. Fifteen smokers were enrolled in this study. Subjects had to be currently smoking and to have relatively normal lung function (forced expiratory volume in 1 second of greater than 80% predicted) at study entry. The subjects received both UTP (45 mg/mL) and placebo (normal saline) three times a day for three consecutive days, with a 1 week wash-out between periods. The purpose of this study was to determine if the highest dose of UTP could be consistently effective in enhancing the amount of sputum expectorated over several consecutive days. This mimics the collection of sputum for the purpose of diagnosing certain lung infections and other conditions which is often done by asking patients to collect their sputum each morning for several consecutive days.

Treatments Assignments and Administration of Study Drug: Each subject was randomly assigned to receive multiple daily doses (three times a day for three consecutive days) of placebo and UTP with at least 1 week between the two dosing periods. Each dose consisted of 4 mL of the 45 mg/mL solution or placebo (normal saline) administered using a jet nebulizer (Pari LC PLUS™) powered by portable compressor (DeVilbiss Pulmo-Aide®) set at 14 L/min. Inhalation of placebo or UTP took approximately 8 to 15 minutes.

Figure 2:
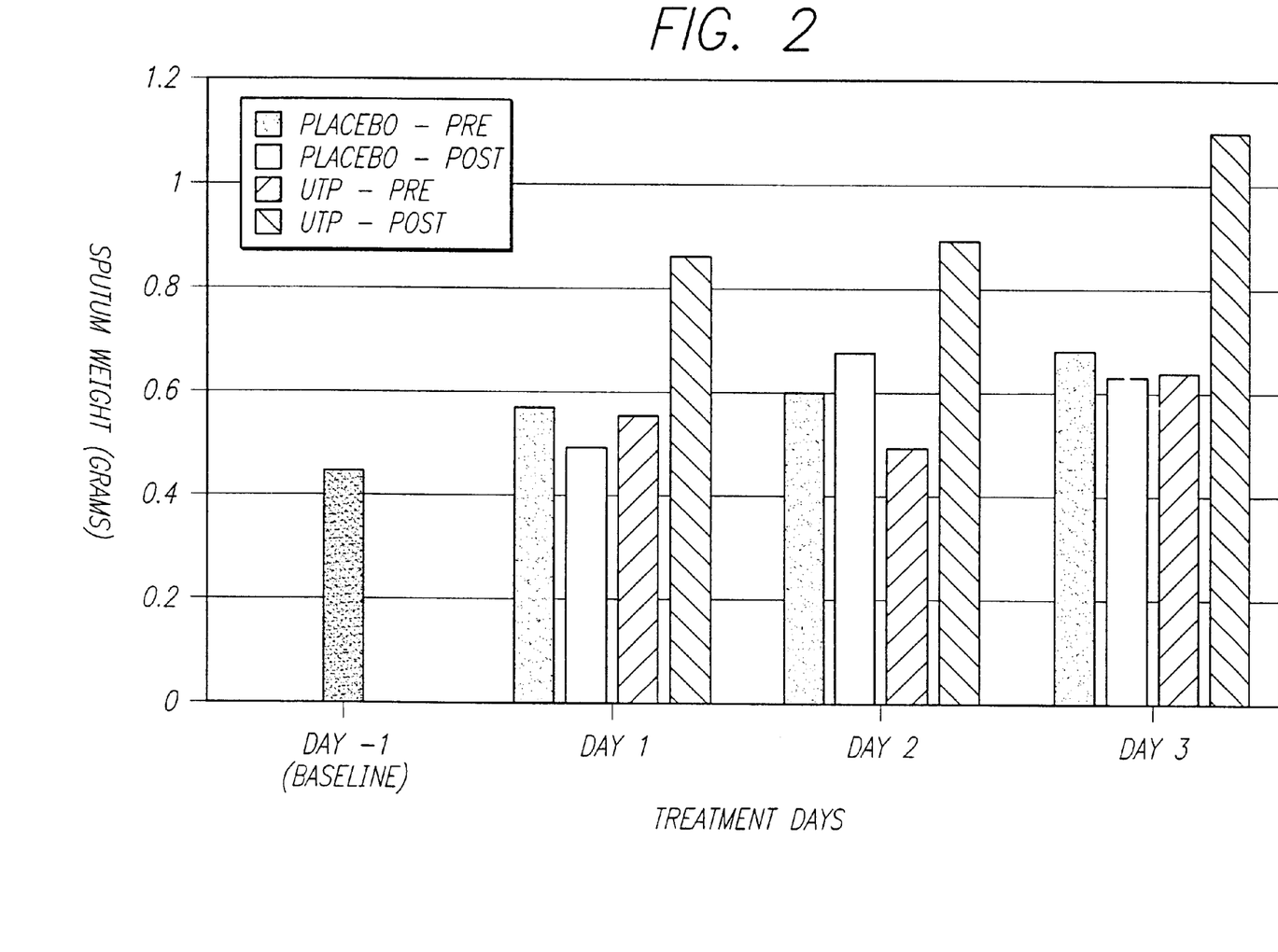
FIG. 2 is a general graphical representation of the effect of UTP Formulation I versus placebo on sputum weights (grams) on three consecutive treatment days in a two-period cross-over study in smokers (n=15).
Figure 3:
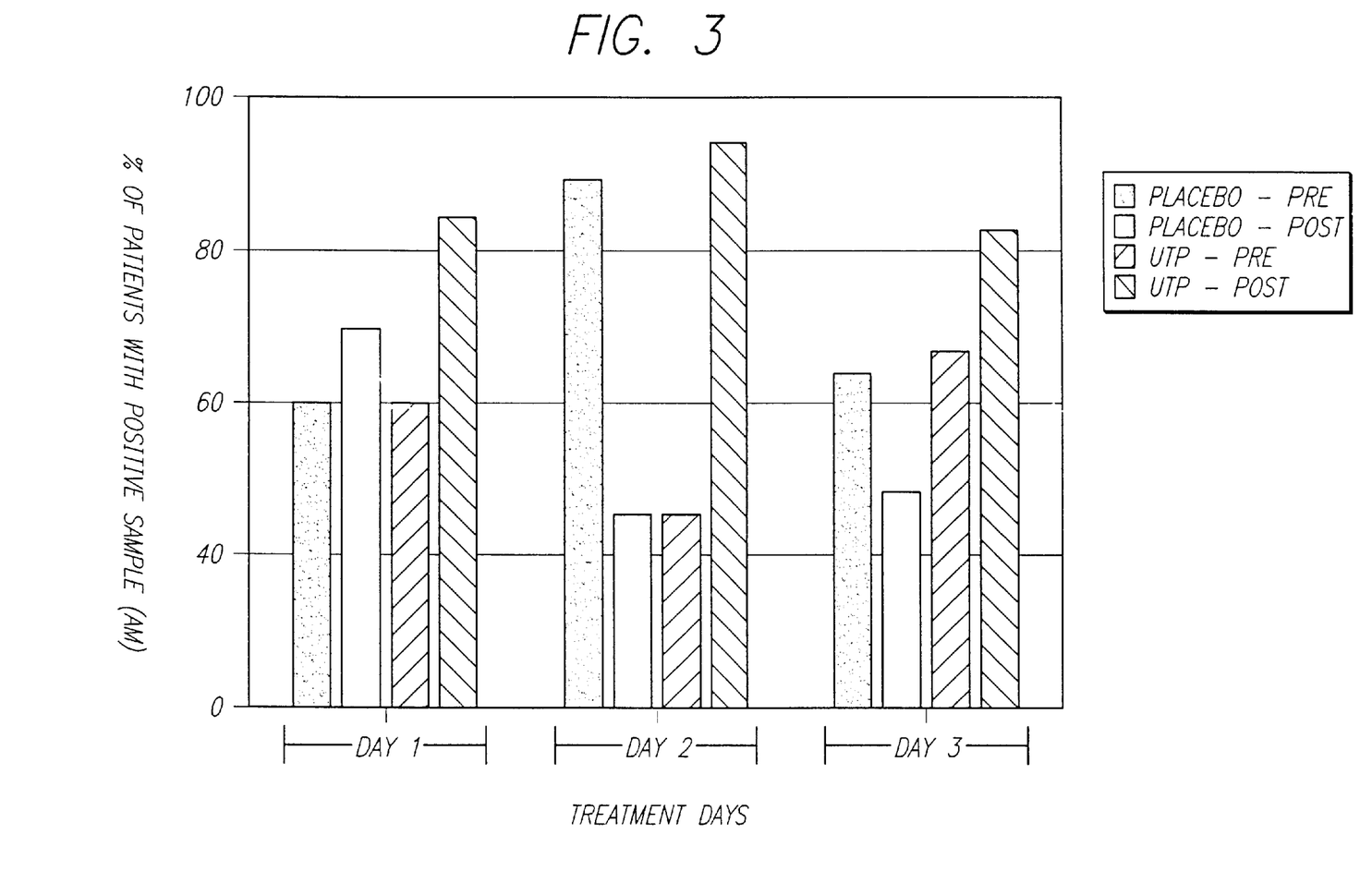
FIG. 3 is a general graphical representation of cytology results on sputum expectorated by smokers receiving UTP Formulation I versus placebo (positive samples defined by the presence of alveolar macrophages, AM) (n=15)

Efficacy Results: The amount of sputum expectorated (weight in grams) was collected pre- and post-dosing of UTP and placebo at various time points across the three days of dosing in each study period. Sputum was also evaluated by cytological examination to determine whether the sputum samples contained alveolar macrophages; indicative of a deep-lung sample. FIG. 2 illustrates the sputum weights (g) at pre-dosing and post-dosing of placebo and UTP over the three days of treatment. As shown in FIG. 2, inhalation of placebo did not increase the amount of sputum expectorated immediately post-dosing during any of the three days of dosing (comparison of sputum weights at pre-dosing to immediately post-dosing). In contrast, inhalation of UTP consistently increased the amount of sputum expectorated immediately post-dosing on all three days of dosing (comparison of sputum weights at pre-dosing to immediately post-dosing); the magnitude of the increase in the amount of sputum expectorated (pre-to post-dosing of UTP) was consistent on each of the three days for the UTP dosing period. FIG. 3 illustrates the cytology data for the sputum expectorated by smokers receiving UTP versus placebo. As shown in FIG. 3, smokers receiving UTP were more likely to produce a sputum sample containing alveolar macrophages (AM) on any of the three days than smokers receiving placebo (the difference between placebo and UTP was most pronounced on Day 2). There appeared to be a trend for placebo to decrease the likelihood of producing a specimen containing alveolar macrophages (comparison of pre-dosing to post-dosing in the placebo group). This study demonstrated that UTP consistently increases the amount of sputum expectorated (that contains alveolar macrophages) over that produced by placebo. This effect of UTP was demonstrated on three consecutive treatment days.

Investigational Products: The test product was UTP Solution for Inhalation in a concentration of 45 mg/mL. UTP solutions were packaged in single use glass vials with rubber stoppers and aluminum tear-off seals. The product was stored refrigerated at 2°–8° C. Each vial delivered 4 mL of solution upon pouring. The pH of each solution was 7.2 and the tonicity of each solution was approximately 300 MOsm/L. Each vial was individually labeled with the contents, strength and storage instructions.

The placebo was supplied as sterile Sodium Chloride Inhalation Solution USP, 0.9% (Dey Laboratories, Napa Calif., USA). Placebo was packaged in single use vials containing 5 mL of solution. Per USP specifications, the pH of the solution was within the range of 4.5–7.0. Four mL of placebo was used for administration. The product was stored at 2°–8° C. Each vial was individually labeled with contents, strength and storage instructions.

C. Clinical Study in Patients with Chronic Bronchitis

This single center study was a randomized, double-blind, crossover evaluation of escalating, single inhaled doses of UTP in patients with chronic bronchitis. Patients enrolled in this study had to meet the American Thoracic Society definition of chronic bronchitis (excessive mucous production over 3 months of the year, for at least 2 successive years). Patients were included that had mild to moderate airflow obstruction (forced expiratory volume over 1 second greater than 65% of predicted at study entry). A total of 26 (14 females and 12 males) patients were enrolled in this study and the majority were currently smoking. Five successive groups of five subjects (an additional patient was added in one cohort due to a drop-out) received a single dose of placebo and the appropriate dose of UTP (2.5, 5, 15, 25, and 45 mg/mL) in a randomized order. The dose of UTP and placebo were separated by at least 24 hours. The purpose of this study was to more carefully define the time course by which UTP enhances the expectoration of sputum in a patient population known to be at high risk for developing lung cancer. In contrast to the previous studies in smokers, the cytologic examination included identification and quantification of both alveolar macrophages as well as respiratory ciliated epithelial cells in the sputum samples.

Treatment Assignments and Administration of Study Drug: Each subject was randomly assigned to receive single inhaled dose of placebo (normal saline) or one of five doses of UTP Formulation I on two separate days. For dosing, each dose consisted of 4 mL of 2.5, 5, 15, 25 and 45 mg/mL solution or placebo administered using a jet nebulizer (Pari LC PLUS) powered by a portable compressor set at 14 L/min. Inhalation of placebo or UTP took approximately 8 to 15 minutes. Investigational Products: The test product was UTP Solution for Inhalation in a concentration of 2.5, 5, 15, 25 or 45 mg/mL. UTP solutions were packaged in single use glass vials with rubber stoppers and aluminum tear-off seals. The product was stored refrigerated at 2°–8° C. Each vial delivered 4 mL of solution upon pouring. The pH of each solution was 7.2 and the tonicity of each solution was approximately 300 MOsm/L. Each vial was individually labeled with the contents, strength and storage instructions.

The placebo was supplied as sterile Sodium Chloride Inhalation Solution USP, 0.9% (Dey Laboratories, Napa Calif., USA). Placebo was packaged in single use vials containing 5 mL of solution. Per USP specifications, the pH of the solution was within the range of 4.5–7.0. Four mL of placebo was used for administration. The product was stored at 2°–8° C. Each vial was individually labeled with contents, strength and storage instructions.

Efficacy Results: The amount of sputum expectorated (weight in grams) was collected at baseline and at various time points post-dosing of UTP and placebo. The time points were: immediately to 5 minutes post-dosing, 6 minutes to 30 minutes post-dosing, and 31 minutes post-dosing to discharge (within several hours of post-dosing). For the purposes of analysis, patients receiving placebo across all dose groups were combined (n=25); patients receiving UTP (all doses) were combined; and patients receiving the three highest dose levels (15, 25 and 45 mg/mL) (n=15) were combined.

Figure 4:
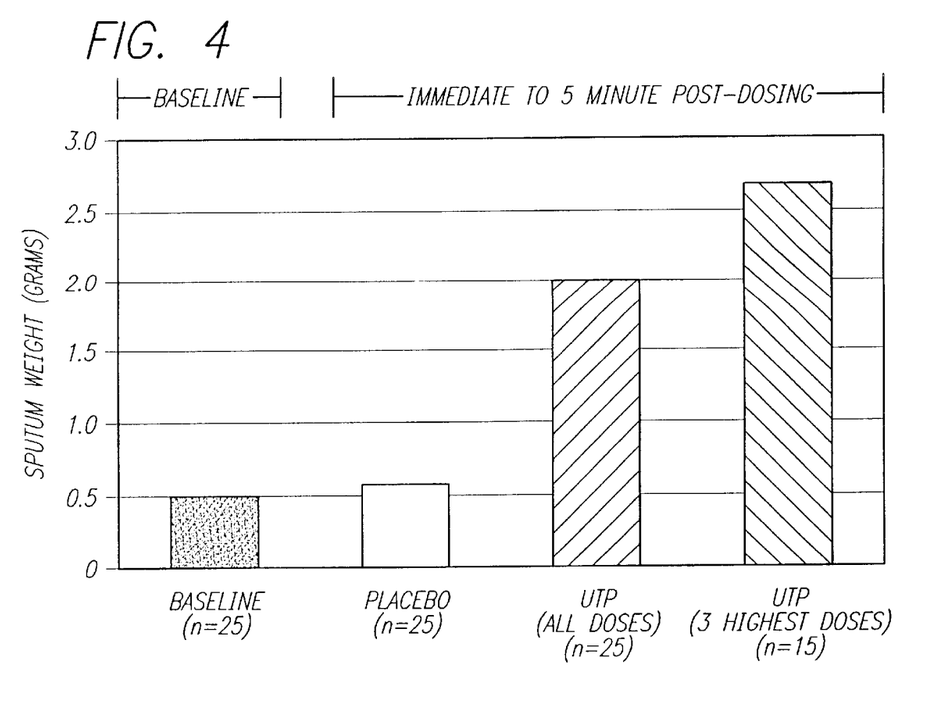
FIG. 4 is a general graphical representation of the effect of UTP Formulation I versus placebo on sputum weights (grams) in patients with chronic bronchitis (baseline versus immediate to 5 minute post-dosing).
Figure 5:
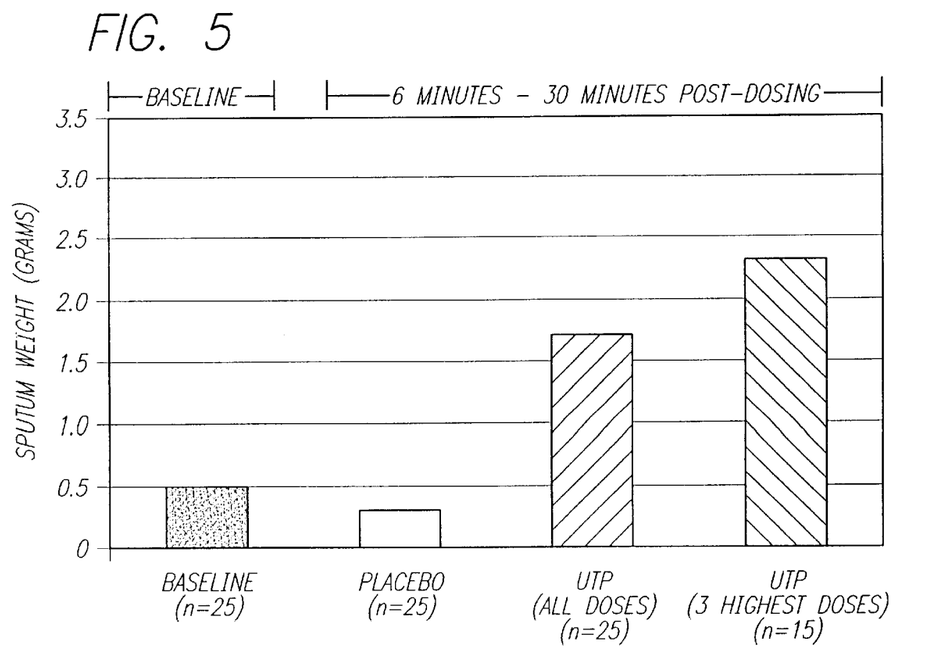
FIG. 5 is a general graphical representation of the effect of UTP Formulation I versus placebo on sputum weights (grams) in patients with chronic bronchitis (baseline versus 6–30 minutes post-dosing).
Figure 6:
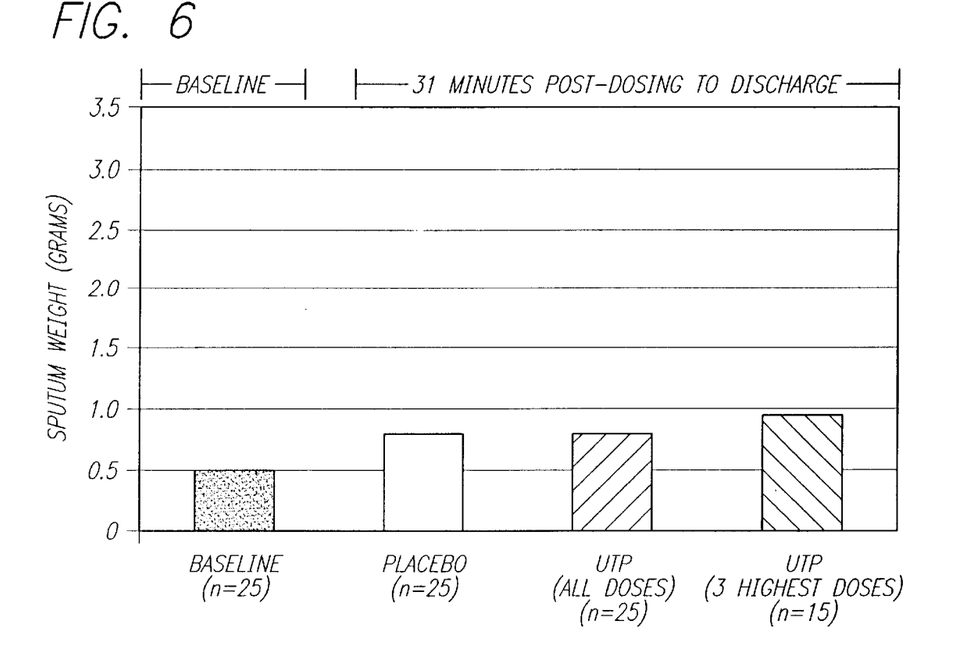
FIG. 6 is a general graphical representation of the effect of UTP Formulation I versus placebo on sputum weights (grams) in patients with chronic bronchitis (baseline versus 31 minutes post-dosing to discharge).

FIG. 4 illustrates the effect of placebo versus UTP on the amount of sputum expectorated (weight in grams) at two time points: baseline (spontaneous expectoration) versus immediately to 5 minute post-dosing. UTP (all doses combined) significantly enhanced the amount of sputum expectorated compared to baseline and placebo (all doses combined). The effect of UTP was even more pronounced when comparing the three highest dose levels of UTP (n=15) to the placebo group. The ability of UTP to enhance the amount of sputum expectorated over placebo and baseline was also evident at the later time point of 6 minutes to 30 minutes post-dosing as shown in FIG. 5. FIG. 6 shows that at the 31 minutes to discharge time point there was essentially no difference between the effect of UTP and placebo on the amount of sputum expectorated, indicating that the effect of UTP is manifested over a short time frame, consistent with the previous studies.

Figure 7:
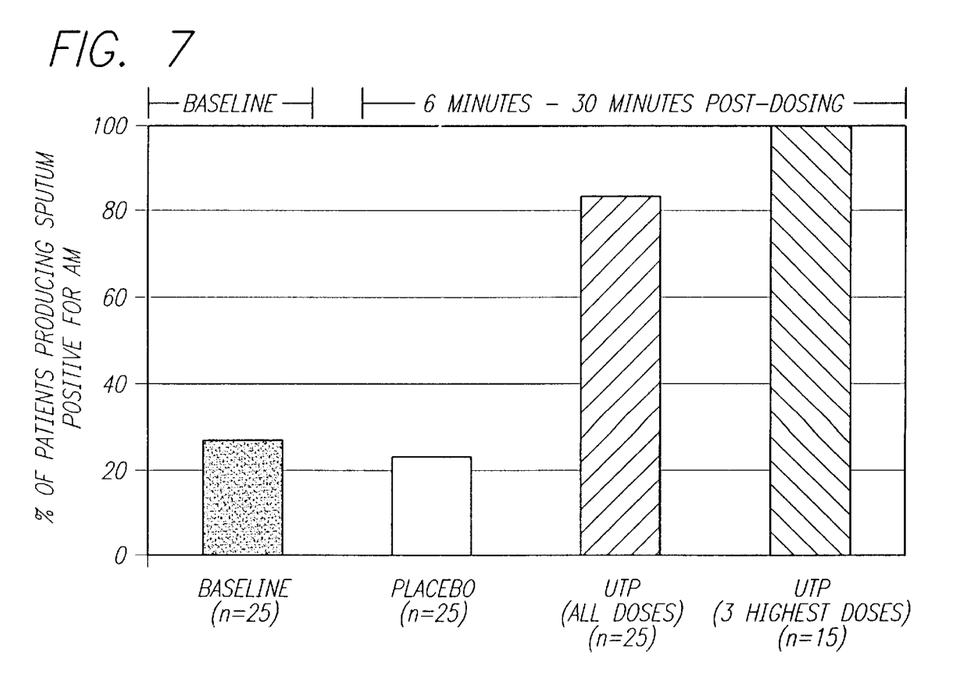
FIG. 7 is a general graphical representation of cytology results from sputum samples collected in patients with chronic bronchitis (positive samples defined by the presence of alveolar macrophages, AM) (baseline versus 6 minutes to 30 minutes post-dosing).
Figure 8:
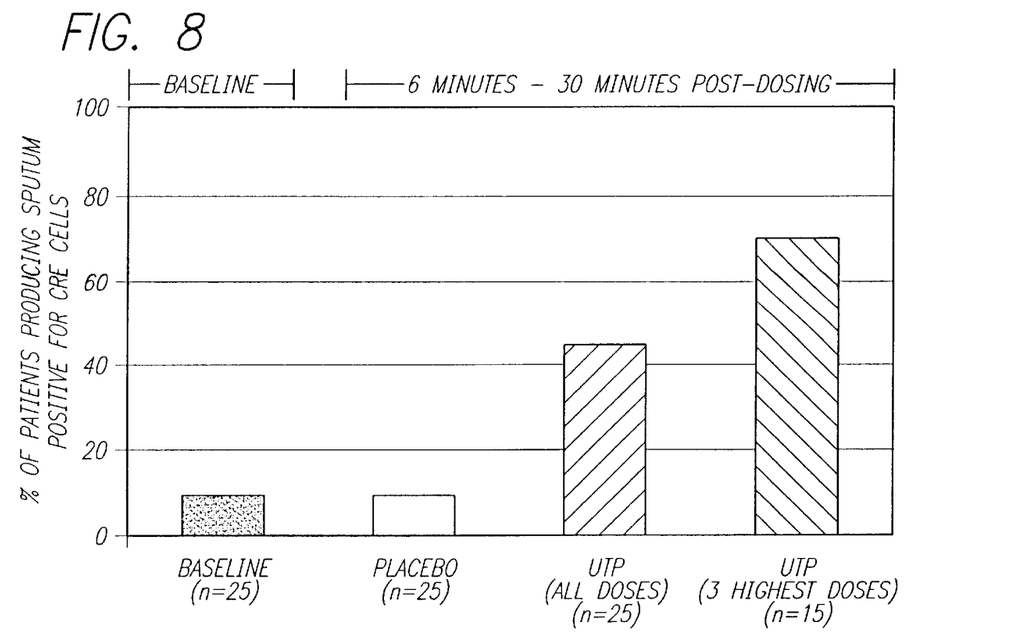
FIG. 8 is a general graphical representation of cytology results from sputum samples collected in patients with chronic bronchitis (positive samples defined by the presence of ciliated respiratory epithelial cells, CRE cells) (baseline versus 6 minutes to 30 minutes post-dosing).

The cytology results from sputum samples collected at the 6 to 30 minutes post-dosing time point are shown in FIG. 7 (sputum containing alveolar macrophages) and FIG. 8 (sputum containing respiratory ciliated epithelial cells). UTP (all doses combined) and UTP (three highest dose levels combined) significantly improved the percentage of patients producing a sputum sample containing alveolar macrophages (AM) compared to placebo (FIG. 7). UTP (all doses combined) and UTP (three highest dose levels combined) also significantly improved the percentage of patients producing a sputum sample containing respiratory ciliated epithelial cells, when compared to placebo (FIG. 8). It is noteworthy in FIG. 8 that only 8% of the patients were able to produce a sample containing ciliated epithelial cells at baseline or after aerosolization of placebo; whereas 73% of the patients could produce such a sample in the UTP (3 highest dose level) group. These effects of UTP were also observed at the immediately to 5 minutes post-dosing time point for alveolar ciliated epithelial cells (baseline/placebo= 8%/4%; UTP (all doses)=32%; UTP (3 highest doses)=50%. The effect of UTP had returned to close to the baseline/ placebo values at the 31 minutes to discharge time point, consistent with the findings on sputum weight.

This study clearly demonstrates that aerosolized doses of UTP (particularly the three highest dose levels of 15, 25 and 45 mg/mL) are more effective than placebo (normal saline) in eliciting the production of deep sputum samples containing cells that could be evaluated for pre-cancerous lesions or changes. Further, UTP can induce the production of a quality sputum sample (containing both alveolar macrophages and ciliated epithelial cells) within a short time frame (within 30 minutes post-dosing).

D. Treatment of a Human Subject with Mild Chronic Bronchitis

It has been demonstrated that two different doses of UTP Formulation I given by inhalation (4 mL of a liquid solution containing either 5 mg/mL or 25 mg/mL UTP) enhances mucociliary clearance over baseline (no inhaled treatment) and also over placebo in a patient with mild chronic bronchitis. In this study, the patient inhaled the different doses of UTP and placebo on separate days. The procedure for measuring mucociliary clearance was accomplished by having the patient inhale, in the following order technetium-labeled iron oxide particles and then either one of the two doses of UTP or placebo. After inhalation of the UTP or placebo, clearance of the radiolabel particles was measured by serial 2-minute gamma scintigraphy images for 2.5 hours. In order to establish baseline mucociliary clearance on the first day of the study, the patient inhaled only the radiolabel and then had the 2.5 hour gamma scintigraphy images performed. Safety data were collected by monitoring heart rate, ECG, blood pressure, oxyhemoglobin saturation by pulse oximetry prior to, during and after inhalation for all dosing periods. During all phases of the study the patient was monitored for any adverse reactions during each dosing period.

Figure 9:
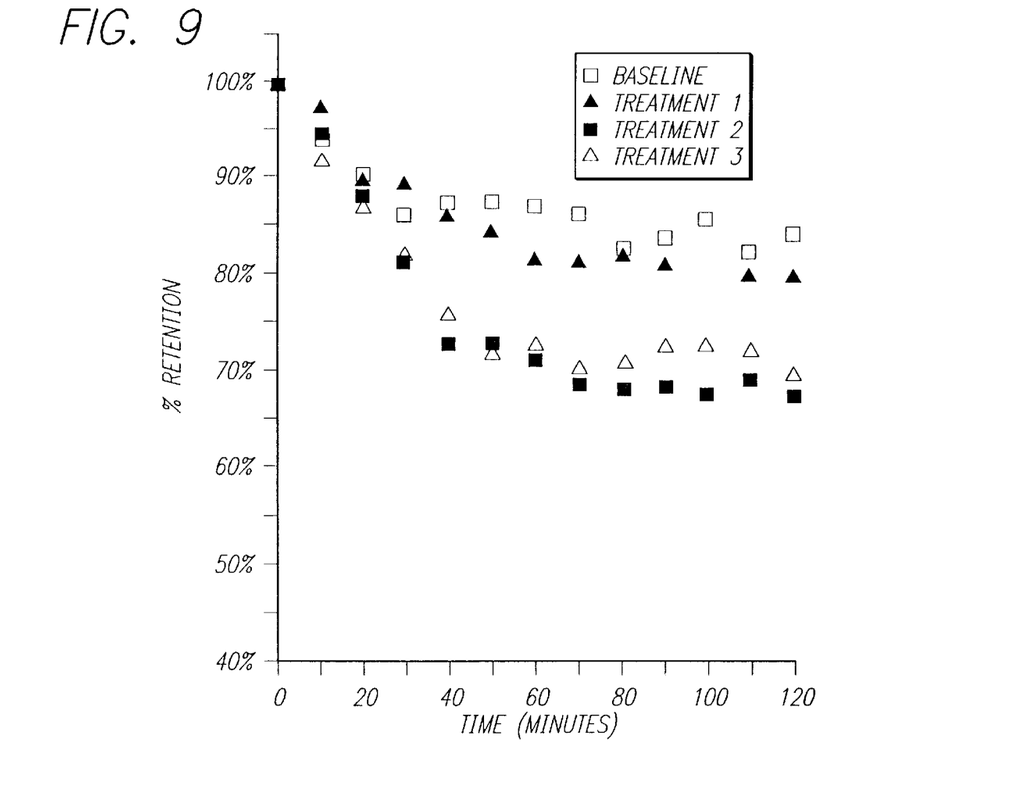
FIG. 9 is a general graphical representation of whole lung retention radiolabel curves for baseline (no inhalation of UTP or placebo), two doses of UTP Formulation I (5 mg/mL is labeled as treatment 3; 25 mg/mL is labeled as treatment 2), and placebo (labeled as treatment 1) over a 2.5 hour time period. A decline in retention demonstrates a clearance of the secretions in the lungs carrying the radiolabel particles.

FIG. 9 shows the whole lung retention curves for baseline (no inhalation of UTP or placebo), both doses of UTP (5 mg/mL is labeled as "treatment 3"; 25 mg/mL is labeled as "treatment 2") and placebo (labeled as "treatment 1") over the 2.5 hour time period. A decline in retention demonstrates a clearance of the secretions in the lungs carrying the radiolabel particles. In this case, both doses of UTP clearly enhanced the clearance of secretions (mucociliary clearance) over placebo and baseline.

Investigational Products: The test product was UTP Solution for Inhalation in a concentration of 5 and 25 mg/mL. UTP solutions were packaged in single use glass vials with rubber stoppers and aluminum tear-off seals. The product was stored refrigerated at 2°–8° C. Each vial delivered 4 mL of solution upon pouring. The pH of each solution was 7.2 and the tonicity of each solution was approximately 300 MOsm/L. Each vial was individually labeled with the contents, strength and storage instructions.

The placebo was supplied as sterile Sodium Chloride Inhalation Solution USP, 0.9% (Dey Laboratories, Napa Calif., USA). Placebo was packaged in single use vials containing 5 mL of solution. Per USP specifications, the pH of the solution was within the range of 4.5–7.0. Four mL of placebo was used for administration. The product was stored at 2°–8° C. Each vial was individually labeled with contents, strength and storage instructions.

Clinical studies in patients with cystic fibrosis (ages 6–40) have shown that UTP Formulation I had no serious adverse effects at dose ranges up to 45 mg/mL.

The invention now being fully described, it will be apparent to one of ordinary skill in the art that changes and modifications can be made thereto without departing from the spirit or scope of the appended claims.

We claim:

1. A sterile pharmaceutical composition comprising uridine 5'-triphosphate (UTP) in a sterile suspension with a concentration of UTP between 45 and 1000 mg/mL, a pH between 6.5 and 12; such that the composition is capable of delivering a therapeutic amount of UTP in a volume range of 10 to 100 µL.

2. A composition according to claim 1 wherein the concentration of UTP is between 100 and 500 mg/mL.

3. A composition according to claim 1 wherein the pH is between 7 and 9.

4. A composition according to claim 1 wherein the volume is between 50 to 100 µL per therapeutic amount.

5. A composition according to claim 1 wherein a preservative is absent.

6. A method of increasing expectoration by administering an amount of a composition according to claims 1–5 effective to increase expectoration.

* * * * *

UNITED STATES PATENT AND TRADEMARK OFFICE
CERTIFICATE OF CORRECTION

PATENT NO. : 5,968,913
DATED : October 19, 1999
INVENTOR(S) : LaCroix, et al.

It is certified that error appears in the above-identified patent and that said Letters Patent is hereby corrected as shown below:

On the title page, item [75]:

In Inventors Section, change "Carey" to --Cary--

Signed and Sealed this

Sixth Day of March, 2001

Attest:

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 5,968,913
DATED : October 19, 1999
INVENTOR(S) : LaCroix, et al.

It is certified that error appears in the above-identified patent and that said Letters Patent is hereby corrected as shown below:

<u>Title page,</u>
Item [75], inventor section, change "Richard C. Evans" to -- Richard M. Evans --.

Signed and Sealed this

Fourteenth Day of August, 2001

*Attest:*

*Attesting Officer*

NICHOLAS P. GODICI
*Acting Director of the United States Patent and Trademark Office*